United States Patent
Xing et al.

(10) Patent No.: US 10,378,028 B2
(45) Date of Patent: Aug. 13, 2019

(54) SYSTEM FOR HYDROGEN PRODUCTION UNDER LIMITED AEROBIC CONDITIONS

(71) Applicants: Defeng Xing, Harbin (CN); Najiaowa Yu, Harbin (CN); Wei Li, Harbin (CN); Zhen Li, Harbin (CN); Yang Yang, Harbin (CN)

(72) Inventors: Defeng Xing, Harbin (CN); Najiaowa Yu, Harbin (CN); Wei Li, Harbin (CN); Zhen Li, Harbin (CN); Yang Yang, Harbin (CN)

(73) Assignee: Harbin Institute of Technology, Harbin, HeiLongJiang (CN)

( * ) Notice: Subject to any disclaimer, the term of this patent is extended or adjusted under 35 U.S.C. 154(b) by 0 days.

(21) Appl. No.: 15/912,385

(22) Filed: Mar. 5, 2018

(65) Prior Publication Data
US 2019/0002924 A1    Jan. 3, 2019

(30) Foreign Application Priority Data

Jun. 29, 2017    (CN) .......................... 2017 1 0512660

(51) Int. Cl.
| | | |
|---|---|---|
| *C12N 1/20* | (2006.01) | |
| *C12P 39/00* | (2006.01) | |
| *C12P 3/00* | (2006.01) | |
| *C12R 1/145* | (2006.01) | |
| *C07C 323/58* | (2006.01) | |
| *C07H 3/02* | (2006.01) | |
| *C07H 3/04* | (2006.01) | |
| *C12R 1/385* | (2006.01) | |

(52) U.S. Cl.
CPC .............. *C12P 3/00* (2013.01); *C07C 323/58* (2013.01); *C07H 3/02* (2013.01); *C07H 3/04* (2013.01); *C12N 1/20* (2013.01); *C12R 1/145* (2013.01); *C12R 1/385* (2013.01)

(58) Field of Classification Search
None
See application file for complete search history.

(56) References Cited

PUBLICATIONS

Xing et al. "Continuous hydrogen production of auto-aggregative Ethanoligenens harbinense YUAN-3 under non-sterile condition" International Journal of Hydrogen Energy 33 (2008) 1489-1495 (Year: 2008).*
Guo et al. "Optimization of culture conditions for hydrogen production by Ethanoligenens harbinense B49 using receptor surface methodology" Bioresource Technology 100 (2009) 1192-1196. (Year: 2009).*
Yoshida et al. "Enhanced biofilm formation and 3-chlorobenzoate degrading activity by the bacterial consortium of *Burkholderia* sp. NK8 and Pseudomonas aeruginosa PAO1" Journal of Applied Microbiology 106(2009) 790-800 (Year: 2009).*
Xing et al. "*Ethanoligenes harvinense* gen. nov. sp. nov, isolated from molasses wastewater." International Journal of Systematic and Evolutionary Microbiology (2006), 56, 755-760 (Year: 2006).*

* cited by examiner

*Primary Examiner* — Blaine Lankford
*Assistant Examiner* — Lauren K Van Buren
(74) *Attorney, Agent, or Firm* — Lili Chen

(57) ABSTRACT

The present invention provides a method for fermentative hydrogen production under limited aerobic conditions by utilizing the respiratory interaction between a strictly anaerobic hydrogen producing bacterium, *E. harbinense* YUAN-3, and a facultative anaerobic bacterium, *P. aeruginosa* PAO1. The two bacteria are co-cultured to produce hydrogen gas in a culture medium without any anaerobic treatment. Sucrose, lactose or glucose are used as the carbon source for the co-culture which can promote the growth of *E. harbinense* YUAN-3 and reduce substrate competition between two bacteria. L-cysteine is added to increase the hydrogen yield and the production rate. Using 15 g/L glucose and 5 mmol/L L-cysteine, the invented method achieved the hydrogen production yield of 1.11 mol-hydrogen/mol-glucose.

9 Claims, No Drawings

SYSTEM FOR HYDROGEN PRODUCTION UNDER LIMITED AEROBIC CONDITIONS

CROSS-REFERENCES AND RELATED APPLICATIONS

This application claims the benefit of priority to Chinese Application No. 201710512660.1, entitled "A system for hydrogen production under limited aerobic conditions", filed Jun. 29, 2017, which is herein incorporated by reference in its entirety.

BACKGROUND OF THE INVENTION

Field of the Invention

The present invention provides a method for hydrogen production under limited aerobic conditions without pH control or immobilizing measures. It is in the field of biological hydrogen production, and is particularly related to the dark-fermentative process.

Description of the Related Art

The traditional methods to remove oxygen for anaerobic bacteria culture include chemical methods (e.g. using chemical compounds with strong reduction potential to absorb the oxygen in the environment or cultural medium, or using reducing agents to reduce the oxidation-reduction potential), physical methods (e.g. using heating, sealing, pumping and other physical methods to scavenge or remove oxygen from the environment or the medium) and biological methods (e.g. using plant tissues to consume oxygen in the culture medium or growing anaerobes and aerobes in the same culture dishes).

Fermentative hydrogen production is a stable and cost-effective technology to produce a clean source of energy, hydrogen, without need of external illumination. In 2005, Xing et al. isolated and established a new ethanol-type fermentative hydrogen production species, *Ethanoligenens harbinense* (*E. harbinense*), and discovered a new strict anaerobic high-efficiency hydrogen producing bacteria strain, *Ethanoligenens harbinense* YUAN-3. It was isolated from hydrogen producing reactor and is the only auto-aggregation hydrogen producing bacteria reported, whose byproducts are ethanol, acetate, carbon dioxide and hydrogen, and can achieve the highest hydrogen yield of 1.9 mol/mol-glucose. However, this process requires continuous boiling and flushing the medium with nitrogen gas or utilizing an expensive anaerobic chamber to remove oxygen. This is not only cumbersome but also not conducive to the expansion of biological hydrogen production.

*Pseudomonas aeruginosa* (*P. aeruginosa*) PAO1 is a facultative anaerobic bacterium widely found in the nature that easily forms a biofilm and can be cultured under aerobic conditions using LB medium in the laboratory.

SUMMARY OF THE INVENTION

In order to solve the problems above, the invention provides a new method for co-culturing an anaerobic hydrogen producing bacterium and a facultative anaerobic bacterium in the medium without anaerobic treatments, which exploits the respiratory interaction of both bacteria to enable culturing the strictly anaerobic hydrogen producing bacterium to produce hydrogen under aerobic conditions.

The method of the invention is to co-culture *E. harbinense* YUAN-3 and *P. aeruginosa* PAO1 to produce hydrogen under aerobic conditions. The co-cultivation is to inoculate the bacterial powder of *E. harbinense* YUAN-3 and *P. aeruginosa* PAO1 into a sterilized liquid medium, and incubate the bacterial culture in a sealed container at 35° C. for 1 to 50 hours, after which the hydrogen starts to be generated and collected. The hydrogen obtained by the method of the invention has both high purity and high yield. The present invention provides a new method for the cultivation of hydrogen-producing bacteria, which is simple to operate and easy to be adapted to large scale production.

DETAILED DESCRIPTION OF THE INVENTION

This goal of the invention is to solve the problem in the existing methods that the hydrogen-producing culture medium needs to be boiled and flushed with nitrogen to exclude oxygen. These are cumbersome and harsh operations that are not easy to be adapted to large scale hydrogen production. Moreover, the boiling and flushing process is likely to cause reagent loss and result in hydrogen impurity. The present invention aims to provide a new method for the cultivation of hydrogen-producing bacteria in limited aerobic conditions. The invention provides a method of co-culturing facultative anaerobic bacteria and strictly anaerobic hydrogen-producing bacteria to produce hydrogen in the culture medium without any anaerobic treatment. The technical details of the invention are described below.

The purpose of the present invention is to provide a method for fermentative hydrogen production under limited aerobic conditions by utilizing the respiratory interaction between *E. harbinense* YUAN-3 and *P. aeruginosa* PAO1.

*E. harbinense* YUAN-3 and *P. aeruginosa* PAO1 are co-cultured. The bacterial powder of *E. harbinense* YUAN-3 and *P. aeruginosa* PAO1 are both inoculated into a sterilized liquid medium, and incubated in a sealed container at 35° C. After 1 to 50 hours, the culture will start to produce hydrogen for collection.

The method of the invention comprises the following steps:

First, perform an anaerobic culture of *E. harbinense* YUAN-3 until white spherical colonies are formed at the bottom of the culture flask and the supernatant become clear. The cultural medium is then centrifuged to collect the cells in the precipitation, and the cells are freeze-dried to obtain *E. harbinense* YUAN-3 powder;

Secondly, perform an aerobic culture of *P. aeruginosa* PAO1 until the absorbance of the broth achieves 0.9 to 1.2 at the wavelength of 600 nm. The culture medium is then centrifuged to collect the cells in precipitation and the cells are freeze-dried to obtain *P. aeruginosa* PAO1 powder;

Thirdly, co-inoculate the *E. harbinense* YUAN-3 and *P. aeruginosa* PAO1 powder (0.1~0.2 g/L-medium *E. harbinense* YUAN-3 and 0.08~0.12 g/L-medium *P. aeruginosa* PAO1) to a sterilized liquid medium and place the sealed culture in a 35° C. incubator. After 1~50 hours of culturing, the hydrogen can be collected.

In one embodiment, 10 g/L to 20 g/L sucrose or lactose or glucose is included in the liquid medium.

In one embodiment, 15 g/L sucrose or lactose or glucose is included in the liquid medium.

In one embodiment, the liquid medium further includes 0-15 mmol/L of L-cysteine.

In one embodiment, 5 to 10 mmol/L of L-cysteine is further included in the liquid medium.

In a preferred embodiment, 5 mmol/L of L-cysteine is also included in the liquid medium.

In one embodiment, 4 g peptone, 1 g yeast extract, 2 g beef extract, 4 g NaCl, 1 g $K_2HPO_4$ and 0.2 g $MgCl_2.6H_2O$ are contained each liter of the liquid medium.

In one embodiment, the inoculation is to add 0.1~0.2 g of *E. harbinense* YUAN-3 and 0.08~0.12 g of *P. aeruginosa* PAO1 per liter of liquid medium.

In one embodiment, the inoculation is to inoculate 0.1 g of *E. harbinense* YUAN-3 and 0.1 g of *P. aeruginosa* PAO1 per liter of liquid medium.

In one embodiment, during the sealed culture, a shaker or a magnetic stirrer is used for mixing the culture.

In one embodiment, the shaking culture condition is to shake at 35° C. with a rotation speed of 170 rpm.

In one embodiment, the magnetic stirrer was stirred under the following conditions: a temperature of 35° C., using a 3 cm magnetic stirrer, and a rotation speed of 70 rpm.

In one embodiment, the bacterial strain of *E. harbinense* YUAN-3 can be obtained through the anaerobic culture method as follows: culturing *E. harbinense* YUAN-3 in a sterilized liquid culture medium. The anaerobic flasks were placed in a shaking incubator at 35° C., shaking at 170 rpm until a white spherical colonies and the supernatant becomes clear at the bottom of the flask. The cultural medium is then centrifuged to collect the cells, and the collected cells are freeze-dried to obtain *E. harbinense* YUAN-3 powder. The culture medium contains 10 g glucose, 3 g peptone, 3 g NaCl, 1 g $K_2HPO_4$, 0.2 g $MgCl_2.6H_2O$, 0.2% resazurin 0.2 mL L-cysteine 0.5 g per liter, with trace elements and vitamins.

In one embodiment, the bacterial powder of the *P. aeruginosa* PAO1 can be obtained through the following aerobic culture method, comprising the steps of: culturing the *P. aeruginosa* PAO1 with a liquid medium sterilized by steaming at a high temperature. The culture flasks is placed in a shaking incubator at 35° C., shaking at 170 rpm until the absorbance (at 600 nm) of the culture broth achieves 0.9 to 1.2. The cultural medium is then centrifuged to collect cells and the collected cells are freeze-dried to obtain *P. aeruginosa* PAO1 powder. The medium contains 10 g peptone, 4 g NaCl, 3 g yeast extract per liter, with trace elements and vitamins.

The invention utilizes facultative bacteria to consume the oxygen in the airtight system to provide a suitable living environment to anaerobic hydrogen-producing bacteria so that the hydrogen-producing bacteria can produce hydrogen in a culture system without anaerobic treatment. The culture system provides sucrose or lactose as the carbon source, which can be utilized only by the hydrogen-producing bacteria, thus reducing the competition for substrate between two bacteria. The L-cysteine used in this invention serves as an important reducing agent which can increase the hydrogen production rate. Compared with the conventional method, the invention avoids the significant loss of the reagents (10%~40%) caused by the boiling and flushing processes.

The Beneficial Effects of the Present Invention

The invention provides a new pathway for culturing hydrogen-producing bacteria. The invention provides a method for co-culturing a facultative anaerobe and a strictly anaerobic hydrogen-producing bacteria in the medium without any anaerobic treatment to produce hydrogen gas. Compared with previous methods, the present invention avoids the boiling and flushing gas processes, therefore preventing the loss of reagents caused by these processes. In the fermentation process, the oxygen in the sealed culture is consumed by the facultative bacteria, resulting in a negative pressure in the sealed system, which is later filled by the generated hydrogen and carbon dioxide so that the generated hydrogen gas is of higher purity and higher yield. Facultative bacteria normally cannot maintain good biological activity at pH<4. But in the present invention, the two selected bacteria show high, sustainable, and stable hydrogen production. Thus no pH regulation is needed. Furthermore, the facultative bacteria *P. aeruginosa* PAO1 employed in the present invention consume oxygen and can form colonies on the surface of the liquid when cultured in the liquid phase, which forms an effective barrier to prevent the oxygen in the air from entering the liquid culture medium. On the other hand, the hydrogen-producing bacteria *E. harbinense* YUAN-3 has the self-agglutination property and can spontaneously form spherical colonies that precipitate to the bottom of the culture medium. Therefore, it does not require additional measures for cell immobilization to prevent bacteria loss, thus lowering the production cost and making it easy to adapt to large scale applications.

The present invention achieves unexpected results by use of sucrose and lactose as the carbon source for co-culturing. It has been reported that *P. aeruginosa* PAO1 oxidizes and decomposes glucose and xylose but does not decompose sucrose and lactose. Therefore, it does not normally occur to technicians to choose sucrose or lactose as substrates. However, the inventors unexpectedly discovered that when using sucrose or lactose as co-culture substrate, *P. aeruginosa* PAO1 not only functions to consume oxygen, but also it reduces substrate competition. Moreover, compared to culturing any of the above bacteria, the substrate utilization rate is increased in co-culture. For example, the utilization rate of mono-culturing *E. harbinense* YUAN-3 is only 80%, but when *E. harbinense* YUAN-3 and *P. aeruginosa* PAO1 are in co-culture, the utilization rate is increased to 99%. This is an unexpected technical effect.

The invention greatly improves the hydrogen production rate and hydrogen yield. Using 15 g/L sucrose as the carbon source with 5 mmol/L L-cysteine, the system begins to produce hydrogen gas after about 20 hours of cultivation and reaches a maximum hydrogen production rate of 72.6 mL/L-medium·h with the average hydrogen evolution rate at 38.3 mL/L-medium·h throughout the process. The final hydrogen yield is 2.58 mol/mol-sucrose.

Increasing the concentration of L-cysteine would increase hydrogen production rate, but may compromise the hydrogen yield. In the present invention, we use the L-cysteine concentration of 5 mmol/L~10 mmol/L which can achieve both a fast hydrogen production rate and a high hydrogen yield. For example, using 10 g/L glucose as substrate, the average hydrogen production rate is 20.3 mL/L-medium·H~26.2 mL/L-medium·h and the maximum hydrogen production rate is 38.7 mL/L-medium·H~50.7 mL/L-medium·h. The hydrogen yield is relatively high too, achieving 0.97~1.05 mol/mol-glucose.

EXAMPLES

The following examples are intended to further illustrate but not limit the scope of the invention.

In the following examples, *E. harbinense* YUAN-3 and *P. aeruginosa* PAO1 were cultivated together.

Example 1. Co-Culture of *E. harbinense* YUAN-3 and *P. aeruginosa* PAO1 Using Sucrose as Carbon Source The present example provides a method for producing hydrogen by use of the respiratory interaction between *E. harbinense* YUAN-3 and *P. aeruginosa* PAO1 as follows:

1) Anaerobic culture of *E. harbinense* YUAN-3: the ethanol-producing strain *E. harbinense* YUAN-3 was inoculated to liquid medium A in an anaerobic bottle, which had been sterilized in high temperature steam, and the anaerobic bottle was placed in a constant temperature shaker whose temperature was 35° C. and the shaking speed was 170 rpm. About 40 hours later, white spherical colonies formed on the bottom of the culture flask and the supernatant became clear. The medium was then centrifuged for 5 minutes at 8000 rpm to collect cells. The collected cells were freeze-dried to obtain *E. harbinense* YUAN-3 powder.

2) Aerobic culture of *P. aeruginosa* PAO1: the *P. aeruginosa* PAO1 was inoculated to liquid medium B which had been sterilized in high temperature steam, and placed in a constant temperature shaker whose temperature was 35° C. and shaking speed was 170 rpm. About 4 hours later, when the absorbance of the culture medium at the wavelength of 600 nm reached 0.9~1.2, the medium was then centrifuged for 5 minutes at 8000 rpm to collect cells. The collected cells were freeze-dried to obtain *P. aeruginosa* PAO1 powder.

3) 0.1~0.2 g/L *E. harbinense* YUAN-3 obtained in step 1) and 0.08~0.12 g/L *P. aeruginosa* PAO1 powder obtained in step 2) were inoculated to the sterilized medium C in a sealed bottle. The bottle was placed in a 35° C. incubator with a multi-channel magnetic stirrer (3 cm magnetic stirrer, speed 170 rmp). The sealed bottle was connected to an airbag via a disposable intravenous infusion needle. Depending on different bacterial growth state, hydrogen gas can be collected 1 to 50 hours after inoculation.

In this example, the mediums A, B and C in steps 1), 2) and 3) were autoclaved at 120° C. for 15 minutes after the medium was prepared.

In the step 1) of this example, the culture time *E. harbinense* YUAN-3 is not limited to 40 hours, the culture should continue until the bacteria form white spherical colonies deposited at the bottom of the culture bottle and the supernatant become clear. The culture solution can then be used for inoculation in the step 3). In the step 2), the culture time of *P. aeruginosa* PAO1 is not limited to 4 hours. The culture solution can be used for inoculation in step 3) when the absorbance of the culture medium at the wavelength of 600 nm reaches 0.9 to 1.2.

The multi-channel magnetic stirrer in the step 3) may also be replaced by a shaker culture method, in which the culture conditions are 35° C. and 170 rpm. The shaker culture method in step 1) and 2) can also be replaced by a magnetic stirring.

Medium A comprises glucose, peptone, NaCl, $K_2HPO_4$, $MgCl_2.6H_2O$, resazurin (0.2% by volume), L-cysteine, vitamins, trace elements and water in step one. For example, one liter medium A may contain 10 g glucose, 3 g peptone, 3 g NaCl, 1.0 g $K_2HPO_4$, 0.2 g $MgCl_2 6H_2O$, 0.2 g resazurin (0.2%), and 0.5 g L-cysteine.

Medium B in step 2) comprises peptone, yeast extract, NaCl, vitamins, trace elements, and water. For example, one liter medium B may contain 10 g peptone, 3 g yeast extract, and 4 g NaCl.

Medium C in step 3) comprises sucrose, peptone, yeast extract, beef extract, NaCl, $K_2HPO_4$, $MgCl_2.6H_2O$, L-cysteine, vitamins, trace elements and water. For example, one liter medium C may contain 10 to 20 g sucrose, 4 g peptone, 1 g yeast extract, 2 g beef extract, 4 g NaCl, 1 g $K_2HPO_4$, 0.2 g $MgCl_2.6H_2O$ and 5 mmol~10 mmol of L-cysteine. High yield of hydrogen can be produced using the conditions above, among which 5 mmol of L-cysteine gives the best result.

In this example, sucrose was 15 g/L and L-cysteine was 5 mmol/L. The other components were as described above.

The trace elements in culture mediums A and C (g/L), are composed of $MgSO_4.7H_2O$ 3, $FeSO_4.7H_2O$ 0.1, $ZnSO_4.7H_2O$ 0.1, $H_3BO_3$ 0.01, $N(CH_2COOH)_3$ 1.5, $CaCl_2.2H_2O$ 0.1, $Na_2MoO_4$ 0.01, $CoCl_2.6H_2O$ 0.1, $NiCl_2.6H_2O$ 0.024, $Na_2WO_4.2H_2O$ 0.025, $MnSO_4.H_2O$ 0.5, $CuSO_4.5H_2O$ 0.01, $KAl(SO4)_2.12H_2O$ 0.01, NaCl 1; vitamins in g/L: riboflavin 0.025, citric acid 0.02, folic acid 0.01, para-aminobenzoic acid 0.01.

Medium A is prepared as follows: first, dissolve all reagents into distilled water except L-cysteine and boil the solution until it turns dark red. Second, after a short cooling, add L-cysteine, mix thoroughly, and continue to boil the solution. After L-cysteine is completely dissolved, add water to make the correct volume. Third, add 100 mL medium A into a 250 mL anaerobic bottle, and use a multi-channel aeration needle to flush high purity nitrogen into the cultural medium until it becomes champagne-colored. Keep flushing nitrogen for five more minutes and then seal the bottle.

Medium B is prepared as follows: dissolve all the reagents into distilled water and split the medium into 150 mL conical flasks, each flask containing 50 mL medium. Seal the bottle with an aseptic breathable film and rubber band.

Medium C is prepared as follows: dissolve all the reagents and then dispense C into 250 mL anaerobic bottles (each bottle contains 100 mL), and seal directly.

In this example, two bacteria were activated successfully in step 1) and 2). Using sucrose as the carbon source in co-inoculation of step 3), hydrogen were collected starting about 20 hours after inoculation and reached peak production in about 40 hours, which was 72.6 mL/L-medium·h. The average hydrogen production rate was 38.3 mL/L-medium·h, and the final yield of hydrogen available was 2.58 mol-hydrogen/mol-sucrose.

In this example, the inoculation in step 3) was carried out by inoculating 0.1 g *E. harbinense* YUAN-3 and 0.1 g *P. aerugisnosa* PAO1 into 1 L liquid medium. These inoculation concentrations give the shortest starting time of hydrogen production. Inoculation can also be carried out by any combination of 0.1~0.2 g *E. harbinense* YUAN-3 and 0.08~0.12 g *P. aeruginosa* PAO1, all of which can result in good hydrogen production.

Example 2. Co-Culture of *E. harbinense* YUAN-3 and *P. aeruginosa* PAO1 Using Lactose as Carbon Source The present example provides a method for producing hydrogen by use of the respiratory interaction between *E. harbinense* YUAN-3 and *P. aeruginosa* PAO1 as follows:

1) Anaerobic culture of *E. harbinense* YUAN-3: the ethanol-producing strain *E. harbinense* YUAN-3 was inoculated to liquid medium A in an anaerobic bottle, which had been sterilized in high temperature steam, and the anaerobic bottle was placed in a constant temperature shaker whose temperature was 35° C. and the shaking speed was 170 rpm. About 40 hours later, white spherical colonies formed on the bottom of the culture flask and the supernatant became clear. The medium was then centrifuged for 5 minutes at 8000 rpm to collect cells. The collected cells were freeze-dried to obtain *E. harbinense* YUAN-3 powder.

2) Aerobic culture of *P. aeruginosa* PAO1: the *P. aeruginosa* PAO1 was inoculated to liquid medium B which had been sterilized in high temperature steam, and placed in a constant temperature shaker whose temperature is 35° C. and shaking speed is 170 rpm. About 4 hours later, when the absorbance of the culture medium at the wavelength of 600 nm reached 0.9~1.2, the medium was then centrifuged for 5 minutes at 8000 rpm to collect cells. The collected cells were freeze-dried to obtain *P. aeruginosa* PAO1 powder.

3) 0.1~0.2 g/L *E. harbinense* YUAN-3 obtained in step 1) and 0.08~0.12 g/L *P. aeruginosa* PAO1 powder obtained in step 2) were inoculated to the sterilized medium C in a sealed bottle. The bottle was placed in a 35° C. incubator with a multi-channel magnetic stirrer (3 cm magnetic stirrer, speed 170 rmp). The sealed bottle was connected to an airbag via a disposable intravenous infusion needle. Depending on different bacterial growth state, hydrogen gas can be collected 1 to 50 hours after inoculation.

In this example, the mediums A, B and C in steps 1), 2) and 3) were autoclaved at 120° C. for 15 minutes after the medium was prepared.

In the step 1) of this example, the culture time *E. harbinense* YUAN-3 is not limited to 40 hours, the culture should continue until the bacteria form white spherical colonies deposited at the bottom of the culture bottle and the supernatant become clear. The culture solution can then be used for inoculation in the step 3). In the step 2), the culture time of *P. aeruginosa* PAO1 is not limited to 4 hours. The culture solution can be used for inoculation in step 3) when the absorbance of the culture medium at the wavelength of 600 nm reaches 0.9 to 1.2.

The multi-channel magnetic stirrer in the step 3) may also be replaced by a shaker culture method, in which the culture conditions are 35° C. and 170 rpm. The shaker culture method in step 1) and 2) can also be replaced by a magnetic stirring.

Medium A comprises glucose, peptone, NaCl, $K_2HPO_4$, $MgCl_2.6H_2O$, resazurin (0.2% by volume), L-cysteine, vitamins, trace elements and water in step one. For example, one liter medium A may contain 10 g glucose, 3 g peptone, 3 g NaCl, 1.0 g $K_2HPO_4$, 0.2 g $MgCl_26H_2O$, 0.2 g resazurin (0.2%), and 0.5 g L-cysteine.

Medium B in step 2) comprises peptone, yeast extract, NaCl, vitamins, trace elements, and water. For example, one liter medium B may contain 10 g peptone, 3 g yeast extract, and 4 g NaCl.

Medium C in step 3) comprises lactose, peptone, yeast extract, beef extract, NaCl, $K_2HPO_4$, $MgCl_2.6H_2O$, L-cysteine, vitamins, trace elements and water. For example, one liter medium C may contain 10 to 20 g lactose, 4 g peptone, 1 g yeast extract, 2 g beef extract, 4 g NaCl, 1 g $K_2HPO_4$, 0.2 g $MgCl_2.6H_2O$ and 5 mmol~10 mmol of L-cysteine. High yield of hydrogen can be produced using the conditions above, among which 5 mmol of L-cysteine gives the best result.

In this example, lactose was 15 g/L and L-cysteine was 5 mmol/L. The other components were as described above.

The trace elements in culture mediums A and C (g/L), are composed of $MgSO_4.7H_2O$ 3, $FeSO_4.7H_2O$ 0.1, $ZnSO_4.7H_2O$ 0.1, $H_3BO_3$ 0.01, $N(CH_2COOH)_3$ 1.5, $CaCl_2.2H_2O$ 0.1, $Na_2MoO_4$ 0.01, $CoCl_2.6H_2O$ 0.1, $NiCl_2.6H_2O$ 0.024, $Na_2WO_4.2H_2O$ 0.025, $MnSO_4.H_2O$ 0.5, $CuSO_4.5H_2O$ 0.01, $KAl(SO4)_2.12H_2O$ 0.01, NaCl 1; vitamins in g/L: riboflavin 0.025, citric acid 0.02, folic acid 0.01, para-aminobenzoic acid 0.01.

Medium A is prepared as follows: first, dissolve all reagents into distilled water except L-cysteine and boil the solution until it turns dark red. Second, after a short cooling, add L-cysteine, mix thoroughly, and continue to boil the solution. After L-cysteine is completely dissolved, add water to make the correct volume. Third, add 100 mL medium A into a 250 mL anaerobic bottle, and use a multi-channel aeration needle to flush high purity nitrogen into the cultural medium until it becomes champagne-colored. Keep flushing nitrogen for five more minutes and then seal the bottle.

Medium B is prepared as follows: dissolve all the reagents into distilled water and split the medium into 150 mL conical flasks, each flask containing 50 mL medium. Seal the bottle with an aseptic breathable film and rubber band.

Medium C is prepared as follows: dissolve all the reagents and then dispense C into 250 mL anaerobic bottles (each bottle contains 100 mL), and seal directly.

In this example, two bacteria were activated successfully in step 1) and 2). Using lactose as the carbon source in co-inoculation of step 3), hydrogen can be collected starting about 40 hours after inoculation and reached peak production in about 160 hours, which was 53.0 mL/L-medium·h. The average hydrogen production rate was 18.6 mL/L-medium·h, and the final yield of hydrogen available was 2.43 mol-hydrogen/mol-lactose.

In this example, the inoculation in step 3) was carried out by inoculating 0.1 g *E. harbinense* YUAN-3 and 0.1 g *P. aerugisnosa* PAO1 into 1 L liquid medium. These inoculation concentrations gave the shortest starting time of hydrogen production. Inoculation can also be carried out using any combination of 0.1~0.2 g *E. harbinense* YUAN-3 and 0.08~0.12 g *P. aeruginosa* PAO1, all of which can result in good hydrogen production.

Example 3: Co-Culture of *E. harbinense* YUAN-3 and *P. aeruginosa* PAO1 Using Glucose as Carbon Source The present example provides a method for producing hydrogen by use of the respiratory interaction between *E. harbinense* YUAN-3 and *P. aeruginosa* PAO1 as follows:

1) Anaerobic culture of *E. harbinense* YUAN-3: the ethanol-producing strain *E. harbinense* YUAN-3 was inoculated to liquid medium A in an anaerobic bottle, which had been sterilized in high temperature steam, and the anaerobic bottle was placed in a constant temperature shaker whose temperature was 35° C. and the shaking speed was 170 rpm. About 40 hours later, white spherical colonies formed on the bottom of the culture flask and the supernatant became clear. The medium was then centrifuged for 5 minutes at 8000 rpm to collect cells. The collected cells were freeze-dried to obtain *E. harbinense* YUAN-3 powder.

2) Aerobic culture of *P. aeruginosa* PAO1: the *P. aeruginosa* PAO1 was inoculated to liquid medium B which had been sterilized in high temperature steam, and placed in a constant temperature shaker whose temperature is 35° C. and the shaking speed is 170 rpm. About 4 hours later, when the absorbance of the culture medium at the wavelength of 600 nm reached 0.9~1.2, the medium was then centrifuged for 5 minutes at 8000 rpm to collect cells. The collected cells were freeze-dried to obtain *P. aeruginosa* PAO1 powder.

3) 0.1~0.2 g/L *E. harbinense* YUAN-3 obtained in step 1) and 0.08~0.12 g/L *P. aeruginosa* PAO1 powder obtained in step 2) were inoculated to the sterilized medium C in a sealed bottle. The bottle was placed in a 35° C. incubator with a multi-channel magnetic stirrer (3 cm magnetic stirrer, speed 170 rmp). The sealed bottle was connected to an airbag via a disposable intravenous infusion needle. Depending on different bacterial growth state, hydrogen gas can be collected 1 to 50 hours after inoculation.

In this example, the mediums A, B and C in steps 1), 2) and 3) were autoclaved at 120° C. for 15 minutes after the medium was prepared.

In the step 1) of this example, the culture time E. harbinense YUAN-3 is not limited to 40 hours, the culture should continue until the bacteria form white spherical colonies deposited at the bottom of the culture bottle and the supernatant become clear. The culture solution can then be used for inoculation in the step 3). In the step 2), the culture time of P. aeruginosa PAO1 is not limited to 4 hours. The culture solution can be used for inoculation in step 3) when the absorbance of the culture medium at the wavelength of 600 nm reaches 0.9 to 1.2.

The multi-channel magnetic stirrer in the step 3) may also be replaced by a shaker culture method, in which the culture conditions are 35° C. and 170 rpm. The shaker culture method in step 1) and 2) can also be replaced by a magnetic stirring.

Medium A comprises glucose, peptone, NaCl, $K_2HPO_4$, $MgCl_2.6H_2O$, resazurin (0.2% by volume), L-cysteine, vitamins, trace elements and water in step one. For example, one liter medium A may contain 10 g glucose, 3 g peptone, 3 g NaCl, 1.0 g $K_2HPO_4$, 0.2 g $MgCl_26H_2O$, 0.2 g resazurin (0.2%), and 0.5 g L-cysteine.

Medium B in step 2) comprises peptone, yeast extract, NaCl, vitamins, trace elements, and water. For example, one liter medium B may contain 10 g peptone, 3 g yeast extract, and 4 g NaCl.

Medium C in step 3) comprises glucose, peptone, yeast extract, beef extract, NaCl, $K_2HPO_4$, $MgCl_2.6H_2O$, L-cysteine, vitamins, trace elements and water. For example, one liter medium C may contain 10 to 20 g glucose, 4 g peptone, 1 g yeast extract, 2 g beef extract, 4 g NaCl, 1 g $K_2HPO_4$, 0.2 g $MgCl_2.6H_2O$ and 5~10 mmol of L-cysteine. High yield of hydrogen can be produced using the conditions above, wherein L-cysteine is between 5-10 mmol and glucose is between 10-20 g/L.

The trace elements in culture mediums A and C (g/L), are composed of $MgSO_4.7H_2O$ 3, $FeSO_4.7H_2O$ 0.1, $ZnSO_4.7H_2O$ 0.1, $H_3BO_3$ 0.01, $N(CH_2COOH)_3$ 1.5, $CaCl_2.2H_2O$ 0.1, $Na_2MoO_4$ 0.01, $CoCl_2.6H_2O$ 0.1, $NiCl_2.6H_2O$ 0.024, $Na_2WO_4.2H_2O$ 0.025, $MnSO_4.H_2O$ 0.5, $CuSO_4.5H_2O$ 0.01, $KAl(SO4)_2.12H_2O$ 0.01, NaCl 1; vitamins in g/L: riboflavin 0.025, citric acid 0.02, folic acid 0.01, para-aminobenzoic acid 0.01.

Medium A is prepared as follows: first, dissolve all reagents into distilled water except L-cysteine and boil the solution until it turns dark red. Second, after a short cooling, add L-cysteine, mix thoroughly, and continue to boil the solution. After L-cysteine is completely dissolved, add water to make the correct volume. Third, add 100 mL medium A into a 250 mL anaerobic bottle, and use a multi-channel aeration needle to flush high purity nitrogen into the cultural medium until it becomes champagne-colored. Keep flushing nitrogen for five more minutes and then seal the bottle.

Medium B is prepared as follows: dissolve all the reagents into distilled water and split the medium into 150 mL conical flasks, each flask containing 50 mL medium. Seal the bottle with an aseptic breathable film and a rubber band.

Medium C is prepared as follows: dissolve all the reagents and then dispense C into 250 mL anaerobic bottles (each bottle contains 100 mL), and seal directly.

In this example, the inoculation in step 3) was carried out by inoculating 0.1 g E. harbinense YUAN-3 and 0.1 g P. aerugisnosa PAO1 into 1 L liquid medium. These inoculation concentrations gave the shortest starting time for hydrogen production. Inoculation can also be carried out by any combination of 0.1~0.2 g E. harbinense YUAN-3 and 0.08~0.12 g P. aeruginosa PAO1, all of which can result in good hydrogen production.

In order to investigate the effect of different glucose concentrations on the hydrogen production, L-cysteine was added at a concentration of 10 mmol/L, and the glucose concentration (g/L) was added at 10, 15 and 20, respectively. The other steps were carried out as described above. The effect of different glucose concentrations on the hydrogen production was shown in Table 1.

TABLE 1

The effect of glucose concentrations on hydrogen production

| Glucose concentration (g/L) | Total hydrogen production time (h) | Maximum hydrogen production rate (mL/L-medium · h) | Hydrogen yield (mol-hydrogen/mol-glucose) | Substrate utilization rate (%) |
|---|---|---|---|---|
| 10 | 45 | 61.2 | 0.97 ± 0.0187 | 99 |
| 15 | 75 | 53.9 | 1.04 ± 0.0908 | 87 |
| 20 | 99 | 42.9 | 0.84 ± 0.0828 | 81 |

As shown in Table 1, substrate concentration can affect yield, substrate utilization rate, and maximum production rate. Increasing the substrate concentration increases the total volume of hydrogen, but the substrate utilization rate and the maximum hydrogen production rate will be adversely affected. In order to obtain higher hydrogen production rate, 15 g/L is the most suitable glucose concentration.

In order to investigate the effects of different concentrations of L-cysteine on the hydrogen production performance, 0.1 g E. harbinense YUAN-3 and 0.01 g P. aeruginosa PAO1 was used for inoculation, 10 g/L glucose was added in the culture medium C. Different L-cysteine concentrations (mmol/L) at 0, 5, 10, and 15 were added in the medium C. The other steps were described in the method above. The effect of L-cysteine concentrations on hydrogen production was shown in Table 2.

TABLE 2

The effect of L-cysteine concentrations on hydrogen production

| L-cysteine concentration (mmol/L) | Hydrogen production begin time (hr) | Time to reach maximum hydrogen production rate (hr) | Total hydrogen production time (hr) | Maximum hydrogen production rate (mL/L-medium · hr) | Hydrogen yield (mol-hydrogen/mol-glucose) |
|---|---|---|---|---|---|
| 0 | 8 | 23 | 120 | 12.5 | 0.51 ± 0.001 |
| 5 | 3 | 35 | 61 | 38.7 | 1.05 ± 0.029 |
| 10 | 5 | 30 | 45 | 50.7 | 0.97 ± 0.0116 |
| 15 | 5 | 24 | 33 | 82.2 | 0.95 ± 0.036 |

It is shown from Table 2 that adding L-cysteine to the co-culture can increase the maximum hydrogen production rate and decrease the starting time for hydrogen production. Maximum hydrogen yield was achieved when 5 mmol/L L-cysteine was added to the co-culture medium.

This example differs from example 1 or 2 in that the concentration of L-cysteine can be adjusted to obtain a higher total production amount at the expense of the yield. When the glucose concentration was 15 g/L and the L-cysteine concentration was 5 mmol/L, the co-culture started to produce hydrogen gas in about 10 hr after inoculation, and the hydrogen yield reached 1.11 mol-hydrogen/mol-glucose.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for hydrogen production under limited aerobic conditions, comprising:
   a. co-culturing *Ethanoligenens harbinense* YUAN-3 and *Pseudomonas aeruginosa* PAO1 in a liquid medium containing 10 to 20 g/L sucrose or lactose as the only carbon source in a sealed container at 35° C.; and
   b. collecting hydrogen gas at 1 to 50 hours after the start of the co-culture.

2. The method of claim 1, wherein the liquid medium contains 15 g/L sucrose as the only carbon source.

3. The method of claim 1, wherein the liquid medium further comprises 0 to 15 mmol/L of L-cysteine.

4. The method of claim 1, wherein the liquid medium further comprises 5 to 10 mmol/L of L-cysteine.

5. The method of claim 1, wherein the liquid medium comprises 5 mmol/L of L-cysteine.

6. The method of claim 1, wherein the liquid medium comprises 4 g peptone, 1 g yeast extract, 2 g beef extract, 4 g NaCl, 1.0 g $K_2HPO_4$ and 0.2 g $MgCl_2.6H_2O$ per liter.

7. The method of claim 1, wherein 0.1-0.2 g of *Ethanoligenens harbinense* YUAN-3 and 0.08-0.12 g of *Pseudomonas aeruginosa* PAO1 are inoculated into the liquid medium.

8. The method of claim 1, wherein during the sealed culture, a shaker or a magnetic stirrer is used for agitation and culture; wherein conditions for culturing using the shaker are: 35° C., rotation speed 170 rpm; and conditions for culturing using the magnetic stirrer are: 35° C., 3 cm magnetic stirrer, stirring speed of 70 rpm.

9. The method of claim 1, wherein the liquid medium contains 10-20 g/L lactose as the only carbon source.

* * * * *